United States Patent

Arlt

[11] 3,962,270
[45] June 8, 1976

[54] PROCESS FOR PREPARING 2-VINYL OXAZOLINES

[75] Inventor: Dieter Arlt, Cologne-Buchheim, Germany

[73] Assignee: Bayer Aktiengesellschaft, Leverkusen, Germany

[22] Filed: May 21, 1974

[21] Appl. No.: 472,016

[30] Foreign Application Priority Data
June 9, 1973 Germany............................ 2329545

[52] U.S. Cl...................... 260/307 F; 260/465.8 R
[51] Int. Cl.²............. C07D 263/12; C07D 263/14
[58] Field of Search................................. 260/307 F

[56] References Cited
UNITED STATES PATENTS
3,505,297   4/1970   Sheetz et al. ...................... 260/78.4
3,813,378   5/1974   Witte et al. .......................... 260/244

OTHER PUBLICATIONS
Purcell—C.A. 65, 12421f (1966).

Primary Examiner—Raymond V. Rush
Attorney, Agent, or Firm—Burgess, Dinklage & Sprung

[57] ABSTRACT

2-vinyl oxazolines having the formula

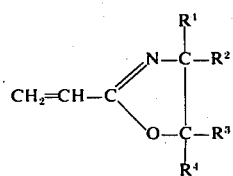

wherein $R^1$, $R^2$, $R^3$ and $R^4$, which may be the same or different, each represents hydrogen, or an optionally substituted alkyl or aryl radical, are prepared by reacting cyclobutane-1,2-dinitrile with an aminoethanol having the formula:

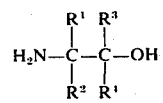

wherein $R^1$, $R^2$, $R^3$ and $R^4$ are as defined at a temperature of from 90° to 180°C and, in a second stage, heating the resulting 1,2-bis-oxazolin-2-yl cyclobutane having the formula:

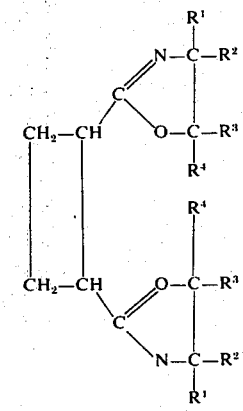

and/or 2-oxazolin-2-yl cyclobutane nitrile having the formula:

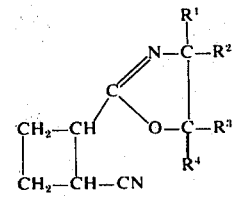

wherein $R^1$, $R^2$, $R^3$ and $R^4$ are defined above, to a temperature of from 250° to 600°C.

3 Claims, No Drawings

PROCESS FOR PREPARING 2-VINYL OXAZOLINES

BACKGROUND

This invention relates to a process for the production of 2-vinyl oxazolines and new substituted 2-vinyl oxazolines.

2-Vinyl oxazoline is valuable comonomer for the production of thermosetting coating compositions (DAS No. 1,261,261). In one known process, the compositions are produced by condensing 2-methyl oxazoline with paraformaldehyde in the presence of strong bases as catalysts to form 2-(2'-hydroxyethyl)-oxazoline from which water is liberated by alkaline catalysts, leaving 2-vinyl oxazoline as the end product. Unfortunately, the yields obtained in both stages only amount to 23 and 64.5%, respectively (cf. angewandte Chemie 78, 922 (1966)). For this reason, it has hitherto only been possible to use 2-vinyl oxazolines on a commercial scale to a limited extent, with the result that there is an urgent need for an improved manufacturing process which is commercially and economically satisfactory.

SUMMARY

It has now been found that 2-vinyl oxazolines corresponding to the formula

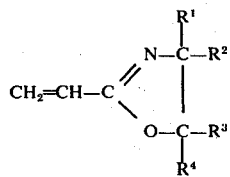

in which $R^1$, $R^2$, $R^3$ and $R^4$, which may be the same or different, each represents hydrogen, or an optionally substituted alkyl or aryl radical, can be obtained in high yields by reacting cis- and/or transcyclobutane-1,2-dinitrile with aminoethanols corresponding to the general formula (I):

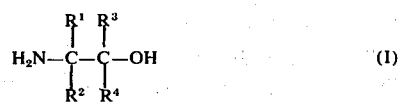

in which $R^1$, $R^2$, $R^3$ and $R^4$ are as defined above, at temperatures of from 90° to 180°C and heating the resulting 1,2-bis-oxazolin-2-yl cyclobutanes corresponding to the general formula (II):

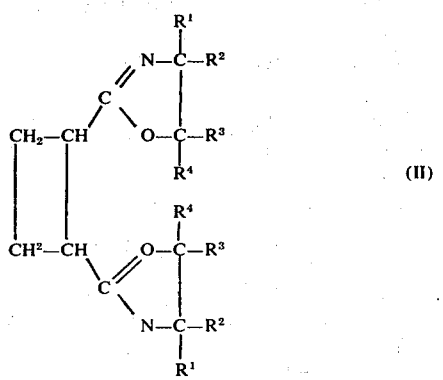

and/or 2-oxazolin-2-yl cyclobutane nitriles corresponding to the general formula (III):

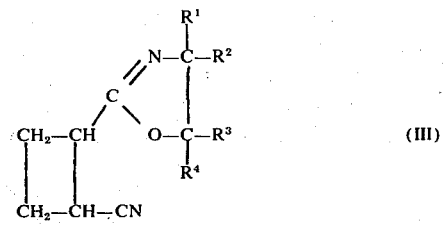

in which $R^1$, $R^2$, $R^3$ and $R^4$ are as defined above, in a second stage to temperatures of from 250° to 600°C.

DESCRIPTION

The product obtained in the first stage is preferably heated to temperatures of from 250° to 550°C, more particularly to temperatures of from 300° to 500°C. Temperatures above 400°C can be applied, especially in cases where it is desired to obtain a high conversion.

The readily polymerising vinyl oxazoline is surprisingly obtained in very good yields and satisfactory purity, despite the high temperatures applied.

In the context of the invention, alkyl radicals are linear or branched alkyl radicals having up to 16, preferably up to 4, carbon atoms, especially methyl and ethyl; the following alkyl radicals are mentioned as examples: propyl, isopropyl, butyl, isobutyl, t-butyl, amyl, isoamyl and the hexyl radicals, the dodecyl and hexadecyl radical.

The hydroxyl group is mentioned in particular as a substituent for the optionally substituted alkyl radicals, the hydroxymethyl group being a particularly preferred substituted alkyl radical.

Aryl radicals are those having 6, 10 or 14 carbon atoms, and may also be substituted by alkyl radicals having 1 to 2 carbon atoms; the phenyl radical is preferred for aryl.

As already mentioned, the process according to the invention is carried out in two stages:

In the first stage, cyclobutane-1,2-dinitrile is reacted with the aminoethanol of general formula (I) by heating to temperatures of from 90° to 180°C. Yields of more than 80% of the theoretical are obtained, even without catalysts.

In general, therefore, there is no need to use any of the catalysts normally used for the reaction of carboxylic acid mononitriles with amino alcohols, these catalysts consisting of a metal salt sufficiently soluble in the reaction medium, whose cation can be lithium, copper, calcium, zinc, cadmium, manganese, nickel or cobalt. However, it can in some cases be advantageous to use catalysts of this kind, especially for shortening the reaction time. It is preferred to use copper (I) chloride, cadmium acetate or zinc acetate.

It is surprising that this reaction should produce such good yields, because it is known that the yields obtained in the production of oxazolines from aliphatic nitriles and aminoethanols are poor and, even when special catalysts are used, are far from satisfactory (cf. DOS No. 2,127,776 and DOS No. 2,135,644). In particular, nitriles of the kind whose nitrile groups are in the 1,2-position have hitherto proved to be unsuitable for synthesising oxazolines in this way (DOS No. 2,135,644, page 4, lines 15 to 18).

In the second stage of the process according to the invention, the compounds of formula (II) and/or formula (III) obtained in the first stage are cleaved under the effect of heat.

The second stage of the process is carried out under normal pressure or reduced pressure, i.e. at pressures in the range of from 0.1 to 760 Torr, preferably in the range of from 1 to 760 Torr, and more particularly in the range of from 15 to 760 Torr.

The reaction can be carried out in a reactor of known type, for example a reaction tube, optionally filled with a conventional inert packing. In general, packing is used to improve the transfer of heat. Examples of suitable packing materials include the conventional packings of quartz, glass, aluminum oxide, iron, clay and active carbon.

To carry out the reaction, the compound of general formula (II) or (III) is generally introduced in liquid form into the heated reactor in which cleavage subsequently takes place, optionally after evaporation. The reaction products leaving the reactor, generally in gaseous form, are subsequently cooled and condensed.

Compounds of general formula (II) and compounds of general formula (III) can be used as the starting compounds for this stage. It is also possible to use mixtures of correspondng, identically substituted compounds of general formulae (II) and (III).

Since the cyclobutane ring is split open, it does not matter whether the compounds of general formulae (II) and (III) have cis- or trans-configuration.

In cases where compounds of general formula (III) are used, acrylonitrile is obtained in addition to the 2-vinyl oxazoline. The acrylonitrile can be separated off from the reaction product, 2-vinyl oxazoline, in known manner, for example by distillation, and can be dimerised almost quantitatively back into the starting material, cyclobutane-1,2-dinitrile, by dimerisation, for example in accordance with the process described in DAS No. 1,081,008, and reused.

Accordingly, it is generally more favourable to carry out the first stage of the process according to the invention in such a way that compounds of general formula (II) are obtained. However, it can also be more favourable, depending upon the amino alcohol used, to carry out the first stage of the process according to the invention in such a way that a compound of general formula (III) or a mixture of corresponding compounds of general formulae (II) and (III) is obtained.

In general, compounds of formula (II) are obtained in cases where the aminoethanol of formula (I) is used in at least the stoichiometrically necessary quantity of 2 mols per mol of cyclobutane-1,2-dinitrile, whereas a mixture of the compounds of formulae (II) and (III) is generally formed in cases where less than the stoichiometrically necessary quantity is used. To prepare compounds of formula (II), it can be advantageous to ue the aminoethanol of formula (I) use an excess of up to 1 mol, more particularly in an excess of from 0.1 to 0.5 mol, over and above the stoichiometrically necessary quantity.

In addition to the known 2-vinyl oxazolines, it is possible by the process according to the invention to obtain novel substituted vinyl oxazolines corresponding to the general formula (IV):

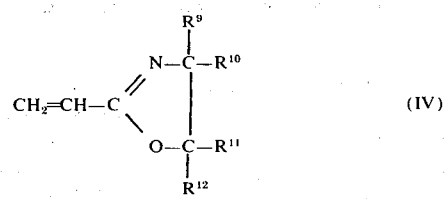

(IV)

in which $R^9$, $R^{10}$, $R^{11}$ and $R^{12}$, which may be the same or different, each represent hydrogen, or an optionally substituted alkyl or aryl radical, at least one of the radicals $R^9$, $R^{10}$, $R^{11}$ or $R^{12}$ containing more than 2 carbon atoms.

The following oxazolines, for example, can be obtained by the process according to the invention: 2-vinyl oxazoline, 2-vinyl-4-methyl oxazoline, 2-vinyl-5-methyl oxazoline, 2-vinyl-5-ethyl oxazoline, 2-vinyl-4,5-dimethyl oxazoline, 2-vinyl-4,4-dimethyl oxazoline, 2-vinyl-5-phenyl oxazoline, 2-vinyl-4-methyl-4-hydroxymethyl oxazoline.

The substituted 2-vinyl oxazolines obtainable by the process according to the invention, and the polymers and copolymers produced from them, differ distinctly in their reactivity from 2-vinyl oxazoline and, as a result, extend the range of potential commercial applications of polymerisable oxazolines.

EXAMPLES

The apparatus used for the following Examples consisted of an upright glass tube, 60 cm long and 2.5 cm wide, and adapted to be heated to the reaction temperature by an electrically heated jacket furnace. The interior of the tube was filled with Raschig rings which occupied about two-thirds of the tube volume, so that approximately 98 ml of the total tube volume of 295 ml was available as the reaction zone. The starting material was introduced in liquid form from the top over a certain reaction time, whilst at the same time a stream of nitrogen was passed slowly through the tube in the tests carried out under normal pressure. The reaction gases were condensed at the lower end in a receiver cooled to −70°C, which was open to the atmosphere so that substantially normal pressure prevailed in the reaction tube.

In the tests carried out under reduced pressure, the receiver was connected to a reduced-pressure system which maintained the reaction pressure in the reaction tube.

Before the beginning of each test, the tube was flushed with nitrogen so that the reaction took place in an inert-gas atmosphere. The following Examples illustrate the invention.

EXAMPLES 1 TO 9

The results of the thermal splitting of 1,2-bis-oxazolin-2′-yl cyclobutane at various temperatures and pressures, and the respective periods of introduction, are shown in Table I below.

TABLE I

| Example No. | Bis-oxazolinyl cyclobutane g | Temperature °C | Pressure Torr | Period of introduction minutes | Yield of 2-vinyl oxazoline g (% of theoretical) | Unreacted starting product*) g | Conversion % |
|---|---|---|---|---|---|---|---|
| 1 | 29.0 | 450 | 760 | 40 | 27.1 (93) | — | — |
| 2 | 26.0 | 450 | 760 | 5 | 17.7 (98.5) | 8.0 | 69 |
| 3 | 24.5 | 450 | 760 | 10 | 23.8 (97) | — | — |
| 4 | 25.0 | 450 | 200 | 4 | 18.0 (97) | 6.5 | 71 |
| 5 | 28.5 | 450 | 15 | 20 | 24.1 (93) | 2.6 | 91 |
| 6 | 30.0 | 400 | 15 | 35 | 18.5 (96) | 10.8 | 64 |
| 7 | 30.0 | 250 | 760 | 40 | 1.0 (91) | 28.9 | approximately 4 |
| 8 | 28.0 | 300 | 760 | 40 | 12.0 (89) | 14.5 | 48 |
| 9 | 30.0 | 500 | 15 | 20 | 10.1 (88) | 18.5 | 38 |

Note
*)1,2-Bis-oxazolin-2'-yl cyclobutane recovered during distillation of the condensate collected in the receiver.

EXAMPLE 10

17 g of 2-oxazolin-2-yl cyclobutane nitrile (boiling point 95 – 97°C/0.1 Torr) were introduced over a period of 20 minutes at 200 Torr/450°C. Distillation of the resulting condensate produced 14.5 g of a mixture of acrylonitrile and 2-vinyl-5-methyl oxazoline, and 1.0 g of starting material. According to analysis by gas chromatography, the mixture substantially consisted of equal molar quantities of the two compounds. This corresponds to a yield of 91% of the theoretical, based on the starting material reacted.

EXAMPLE 11

35 g of 1,2-bis-(5-methyl oxazolin-2-yl)-cyclobutane (boiling point 109° – 112°C/0.1 Torr) were introduced over a period of 16 minutes under a pressure of 200 Torr and at a reaction temperature of 450°C. Distillation of the resulting condensate gave 4.9 g of starting material and 27.6 g of 2-vinyl-5-methyl oxazoline boiling at 36° to 37°C/12 Torr. This corresponds to a yield of 92% of the theoretical, based on the starting material reacted.

2-Vinyl-5-methyl oxazoline shows sharp absorption bands at 1660, 1640 and 1596 cm$^{-1}$.

EXAMPLE 12

30.5 g of 1,2-bis-oxazolin-2-yl cyclobutane were introduced into the test apparatus over a period of 35 minutes at a temperature of 400°C and an average pressure of 760 Torr, whilst at the same time a stream of nitrogen was passed through at a rate of 5.8 ml/second. Accordingly, the average residence time of the starting material in the reaction tube amounted to approximately 17 seconds.

Distillation of the condensate obtained gave 18.7 g of 2-vinyl oxazoline and 11.2 g of starting material, which corresponds to a conversion of 63% and a yield of 97% of the theoretical, based on the conversion.

If the rate of flow of the nitrogen is reduced by half, i.e. to 2.9 ml/second, i.e., if the average residence time is doubled, i.e., to approximately 34 seconds, the condensate obtained gives, by distillation, 25.2 g of 2-vinyl oxazoline and 4.2 g of starting material. This corresponds to a conversion of 86% and to a yield of 96% of the theoretical, based on the conversion.

EXAMPLE 13

30 g of 1,2-bis-(4-methyl-4-hydroxymethyl oxazolin-2-yl)-cyclobutane were introduced into the apparatus described above (at room temperature) together with an 8.3 ml/second stream of nitrogen, and the compound was thermally decomposed at a temperature of 450°C and a pressure of 760 Torr. Fractional distillation of the resulting condensate gave, in addition to 3 g of starting material, 23.4 g (87% of the theoretical) of 2-vinyl-4-methyl-4-hydroxymethyl oxazoline boiling at 75°C/0.3 Torr.

The starting material used, namely 1,2-bis-(4-methyl-4-hydroxymethyl oxazolin-2-yl)-cyclobutane was obtained in accordance with Example 16.

EXAMPLES 14 TO 16 (reaction of cyclobutane-1,2-dinitrile with aminoethanols of formula (I)).

EXAMPLE 14

80 g of cyclobutane-1,2-dinitrile (cis, trans-mixture) were heated for 2.5 hours to 100°C with 101 g of 2-aminoethanol, ammonia being given off. The reaction product was distilled off from the reaction vessel (boiling range about 100° – 160°C/1.5 Torr) and was subsequently fractionated in a Vigreux colunm. 1,2-Bis-(oxazolin-2-yl)-cyclobutane boiling at 114° – 117°C/0.06 Torr was obtained in a yield of 118 g (81% of the theoretical).

EXAMPLE 15

53 g of cyclobutane-1,2-dinitrile were heated for 5 hours to 150°C with 80 g of 1-amino-2-propanol, ammonia being given off. The reaction mixture was introduced dropwise into a vacuum distillation apparatus whose distillation retort was kept at 200 to 225°C, at a rate commensurate with the distillation rate. The reaction product distilled at 124° – 150°C/1.5 Torr, 121 g of distillate being obtained.

Fractionation of this distillate in a Vigreux column gave 20 g (24.5% of the theoretical) of 2-(5-methyl oxazolin-2-yl)-cyclobutane nitrile boiling at 95 – 97°C/0.1 Torr and 71 g (64% of the theoretical) of 1,2-bis-(5-methyl oxazolin-2-yl)-cyclobutane boiling at 110° – 112°C/0.08 Torr.

EXAMPLE 16

53 g of cyclobutane-1,2-dinitrile were heated for 3.5 hours to 100°C with 150 g of 2-hydroxymethyl-2-amino-1-propanol in the presence of 0.5 g of CuCl. Distillation of the reaction mixture in the same way as described in Example 15 gave 175 g of distillate boiling at 142° – 200°C/0.6 Torr which, when subsequently fractionated in a Vigreux column, gave 117 g (83% of the theoretical) of 1,2-bis-(4-methyl-4-hydroxymethyl oxazolin-2-yl)-cyclobutane boiling at 198° – 204°C/0.05 Torr.

What is claimed is:

1. Process for preparing 2-vinyl oxazolines having the formula

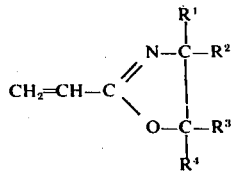

wherein $R^1$, $R^2$, $R^3$ and $R^4$, which may be the same or different, each represents hydrogen, alkyl with up to 4 carbon atoms, hydroxy substituted alkyl with up to 4 carbon atoms, phenyl and phenyl substituted by alkyl with 1 to 2 carbon atoms which comprises the steps of reacting in a first stage cyclobutane-1,2-dinitrile with an aminoethanol having the formula:

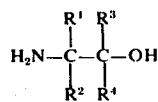

wherein $R^1$, $R^2$, $R^3$ and $R^4$ are as defined at a temperature of from 90° to 180°C and, in a second stage, heating the resulting 1,2-bis-oxazolin-2-yl cyclobutane having the formula:

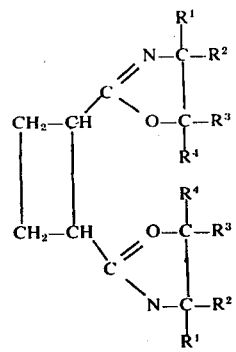

and/or 2-oxazolin-2-yl cyclobutane nitrile having the formula:

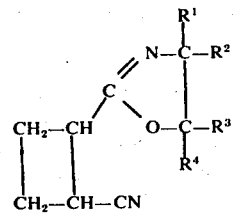

wherein $R^1$, $R^2$, $R^3$ and $R^4$ are defined above to a temperature of from 250° to 600°C.

2. Process of claim 1 wherein the first stage is catalyzed by a metal salt whose cation is selected from the group of lithium, copper, calcium, zinc, cadmium, manganese, nickel and cobalt.

3. Process of claim 2 wherein the catalyst is selected from the group of copper chloride, cadmium acetate and zinc acetate.

* * * * *